United States Patent [19]

Alexander et al.

[11] Patent Number: 5,070,866
[45] Date of Patent: Dec. 10, 1991

[54] WOVEN BACK SUPPORT BELT WITH RIGIDITY CONTROL

[76] Inventors: William K. Alexander, 8425 Dresden Dr., Knoxville, Tenn. 37923; Jack R. Miller, Sr., 242 Piney Mountain, Greenville, S.C. 29609

[21] Appl. No.: 604,750
[22] Filed: Oct. 25, 1990
[51] Int. Cl.⁵ .......................... A61F 5/02; A61F 5/37; A41B 3/00
[52] U.S. Cl. ...................................... 128/78; 128/876; 2/311
[58] Field of Search ............ 2/311, 312, 318, 338–339; 128/876, 78, 89 R, 90; 273/123, 141

[56] References Cited

U.S. PATENT DOCUMENTS

| | | | |
|---|---|---|---|
| 3,921,222 | 11/1975 | Hollman | 128/78 |
| 4,390,014 | 6/1983 | Forman | 128/78 |
| 4,745,911 | 5/1988 | Bender | 128/78 |
| 4,798,200 | 1/1989 | Warthen | 128/89 R |
| 4,907,576 | 3/1990 | Curlee | 128/78 |

Primary Examiner—Robert A. Hafer
Assistant Examiner—Michael Brown
Attorney, Agent, or Firm—Luedeka, Hodges, Neely & Graham

[57] ABSTRACT

A semi-flexible back support belt with selective rigidity control. The belt is formed primarily of a multiple-ply webbing of woven polymeric material. The plies in this webbing are joined together by longitudinally extending binder yarns in a weave pattern which ties together the plies of the webbing in such a manner as to provide a hinging action within the webbing during the application of a longitudinally applied tensile loading on the webbing as provided by the tightening of the belt about the waist of the user which effectively increases the rigidity of the belt. The loosening of a previously tightened belt will decrease the rigidity of the belt. By selectively varying the user applied tensile loading on the webbing, the belt is provided with a wide range of rigidity levels.

22 Claims, 2 Drawing Sheets

WOVEN BACK SUPPORT BELT WITH RIGIDITY CONTROL

FIELD OF INVENTION

The present invention relates generally to a woven semi-flexible support device with rigidity control, and more particularly to a semi-flexible back support belt of woven polymeric material in which the rigidity of the belt is selectively controlled by varying a user applied longitudinal tensile loading on the belt.

BACKGROUND OF INVENTION

Participation in various sporting events and professions such as weight lifting, motor cross, heavy equipment operation, construction, and the like often places a considerable strain on the lower back. Efforts to alleviate such back strain problems have been satisfactorily achieved through the use of stiff, heavy leather belts which are placed about the waist of the participants prior to engaging in activities such as mentioned above, where conditions conducive to back strain may be present. Such leather belts are commercially available in various widths and thicknesses so that a belt with a suitable level of rigidity can be provided for back supporting purposes required for participation in a particular activity by a particular person.

Studies have shown also that the wearing of a properly designed lumbar-abdominal support belt can significantly reduce the risk of back injuries among industrial workers, especially in combination with the practice of good body mechanics, generally accepted lifting techniques and sound physical conditioning. Such belts have been demonstrated to increase the intra-abdominal pressure (IAP) by aiding in the compression of the contents of the abdominal compartment, thereby allowing it to bear some of the load that would otherwise contribute to spinal compression. As the abdominal compartment supports some of the load, the muscles of the lower back are also relieved. IAP can reduce the compressive force acting on the lumbar spine by up to fifty percent (50%). Spinal disc compression is said to be the leading cause of disc deterioration. Industrial users of properly designed belts have shown reductions of up to forty percent (40%) in the incidence of disabling back injury. And, these same users reported that both the severity and duration of back injuries has been reduced considerably when personnel wear support belts. Properly designed belts are those belts which are fitted to the individual user in a manner that permits the selection by the user of the degree of support required for the task at hand.

However, it has been found that the wearing of a leather belt with a "built-in" rigidity factor is not necessarily desirable or suitable for a person engaging in different levels of any one activity. For example, in weight lifting events some lifts require a greater level of back support than in other lifts even in the same type lift depending upon the weight being lifted and the physical makeup of the lifter. Some lifters attempt to overcome these differing requirements for back support by varying the tightness of the belt about their waist. At best, this makeshift solution is minimally satisfactory. Further, the stiffness of the leather belts prevent the belts from substantially conforming to the shape of the body of any particular user so as to be uncomfortable in most instances. In fact, when the leather belts are tightened about the waist of the user they are very unyielding and substantially inhibit body movement. Thus, considerable shortcomings or drawbacks are present in the use of the inflexible and uncomfortable leather belts of fixed rigidity especially since each belt is particularly suitable for only one or a very limited number of back supporting conditions so as to require a considerable number of belts of different rigidity for participation in activities such as weight lifting.

SUMMARY OF THE INVENTION

Accordingly, it is an object of the present invention to provide a back support device or belt wherein the rigidity of the belt can be selectively controlled by the user so that a single belt may be used in activities requiring different levels of rigidity for back support.

Another object of the present invention is to provide a semi-flexible belt wherein the level of rigidity is easily adjusted over a wide range of rigidity levels by the tightening or the loosening of a previously tightened belt about the waist of the belt user.

Another object of the present invention is to provide a semi-flexible back support belt which substantially conforms to the body shape of the user even during different levels of user-induced rigidity so as to be substantially more comfortable and yielding than the stiff and cumbersome leather belts utilized for back support purposes.

Another object of the present invention is to provide a semi-flexible belt constructed of multiple layers or plies of woven polymeric material with the plies interconnected in such a manner that changes in user-applied, longitudinal tensile loadings in the belt effectively vary the closeness which contiguous plies are pressed or pulled together through a "hinging" action in the belt to control the rigidity of the belt.

Generally, the semi-flexible support device with controlled rigidity as envisioned by the present invention comprises an elongated or longitudinally extending semi-flexible back support belt having selective rigidity control. This belt comprises a webbing formed of a plurality of contiguous plies of woven yarns with each ply comprising a plurality of longitudinally extending warp yarns interlaced with transversely extending weft yarns. Binder yarn means comprising a plurality of longitudinally extending yarns selectively engage weft yarns in the webbing for coupling together the webbing plies and for providing hinge means which is used to control the rigidity of the belt. The hinge means is activated by selectively applying a longitudinally tensile loading on the webbing which, through the hinge means, pulls the plies increasingly closer together to thereby selectively increase the rigidity of the webbing and thus that of the belt. Adjustable means are carried by the webbing for applying a selected longitudinal tensile loading on the webbing to provide the belt with a selected rigidity.

Applicants have discovered that interconnecting the contiguous plies of a multiple-ply webbing belt, employing several longitudinally extending binder, i.e. warp, yarns, which extend between and engage weft yarns of selected plies, provides a hinge-like arrangement between plies of the multiple-ply webbing whereby a longitudinally applied tensile loading on the belt causes the binder to foreshorten and the plies to be pulled closer together to effectively increase the longitudinal and transverse rigidity over that inherently provided in the belt by the multiple ply webbing. Thus, by simply varying the longitudinal tensile loading on the belt webbing by employing a suitable buckle or fastening arrangement, the rigidity of the belt can be selectively controlled to a level of rigidity desired by the user.

Other and further objects of the present invention will become obvious upon an understanding of the illustrative embodiment about to be described or will be indicated in the appended claims and various advantages not referred to herein will occur to one skilled in the art upon employment of the invention in practice.

A preferred embodiment of the invention has been chosen for purposes of illustration and description. The preferred embodiment is not intended to be exhaustive nor to limit the invention to the precise form disclosed. It is chosen and described to best explain the principles of the invention and their application and practical use to thereby enable others skilled in the art to utilize the invention in various embodiments and modifications that are adapted to the particular use contemplated. Thus, while the belt as illustrated and described herein comprises a four-ply primary belt webbing and a two-ply belt fastening webbing, it will appear clear that belts with primary webbings and fastening webbings may be formed with webbings containing different numbers of plies which can satisfactorily incorporate the features of the present invention. For example, a multiple-ply primary belt webbing formed of a number of plies in the range of two to six plies may be satisfactorily employed in the practice of the present invention. Also, if desired, the belt fastening webbing may comprise a webbing with greater than the two plies described herein. Further, while the plain weave pattern is the preferred weave for forming the belt webbing and the belt fastening webbing, it will appear clear that other weave patterns such as twill weave, semitwill, or other more complex weave patterns may be satisfactorily used in the practice of the present invention. Many of these variables depend upon the weight and type of yarns used, the width of the belt, and the belt rigidity required by the user, and the economics associated with the manufacture of the belt.

DETAILED DESCRIPTION OF THE INVENTION

As generally described above, the present invention is directed to a semi-flexible support belt formed of multiple plies of webbing of polymeric material wherein the plies are tied together by binder yarns which extend longitudinally and are interwoven with the weft yarns contained in the several plies of the webbing in such a manner so as to provide a ply-joining arrangement having a hinging action which provides the belt with selective rigidity upon applying a longitudinally directed tensile loading on the webbing.

Figure 1:
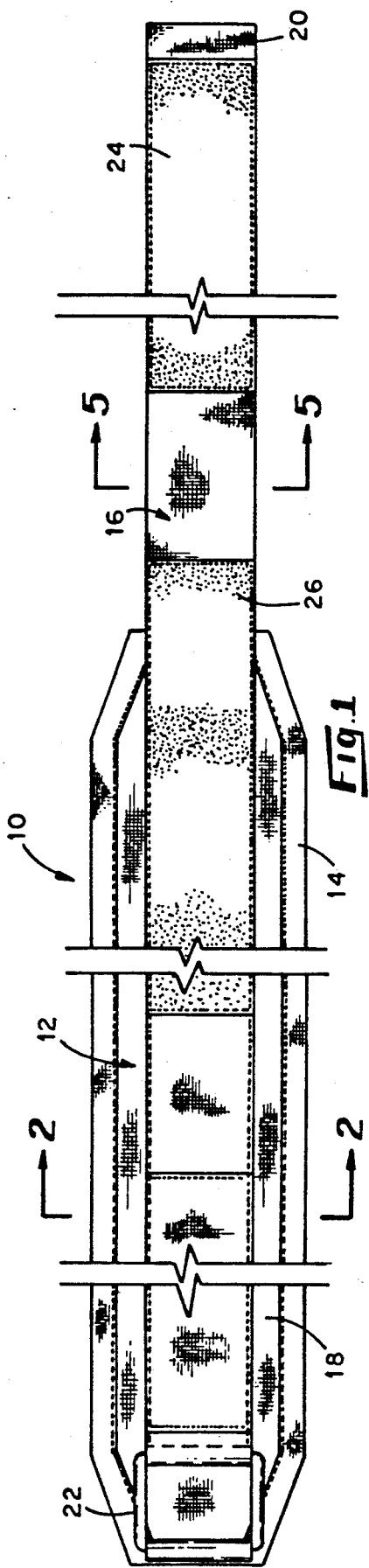
FIG. 1 illustrates an embodiment of a semi-flexible support belt which is characterized by selective rigidity control in accordance with the principles of the present invention.

With reference to the accompanying drawings where like features are identified with similar numerical designations, FIG. 1 illustrates a back support belt 10 constructed in accordance with the present invention. The belt 10 is shown comprising a longitudinally extending primarily webbing 12 formed of multiple layers or plies which are tied together by longitudinally extending binder yarns to provide a belt-rigidizing hinge arrangement as will be described below. The webbing 12 is readily provided in any longitudinal length which will generally correspond to the girth of the belt user. The length of the webbing 12 is preferably slightly less than that required to encompass the waist of the user so that the belt may be securely fastened to the body of the user without overlapping the ends of the belt.

The peripheral sides or edges of the belt 10 are preferably formed with a suitable binding 14 stitched onto the webbing 12 with any suitable thread such as nylon. This binding web may be formed of any suitable yarn such as a natural polyester yarn woven in a plain weave pattern with warp yarns and weft yarns of suitable weights such as respectively provided by 1000/1 denier yarn and 220/1 denier yarn. The binder yarns for this belt binding web 14 may be readily provided by a natural polyester yarn of 500/1 denier. While these particular yarn weights and material are preferred, it will appear clear that the yarns in binding webbing 14 may be made of any suitable material and of any suitable weight and weave. This belt binding webbing 14 is normally of a width of about one inch so that it can overlap the front or face and the back of the belt webbing 12 and is of a sufficient length so as to extend around the peripheral edges of the belt webbing 12.

The belt 10 is shown provided with a longitudinally extending strap or fastening webbing 16 which is stitched to the belt 10 with a suitable thread such as nylon so as to be longitudinally oriented and centrally supported on the outermost surface or face 18 of the webbing 12. This webbing strap 16, as will be described in greater detail below, is provided with a free or unattached end portion 20 which extends beyond one end of the belt webbing 12 a distance of about 12 to 24 inches. The other end of the webbing strap 16 is provided with a suitable loop or buckle 22 through which the free end portion 20 is passed and pulled thereagainst to tighten the belt about the waist of a user. This tightening of the belt applies a selected longitudinal tensile loading onto the webbing 12 through the webbing strap 16 to effectively control the rigidity of the belt to a sufficient level to provide the back support needed or required by the user.

The belt 10 may be of any desired width considered practical for the particular use envisioned. For example, a narrow belt having a width of about 2 inches may be satisfactory to provide back support in relatively minor backstrain inducing events where back support requirements are minimal, whereas a wider belt having a width in the range from 2 to about 8 inches may be desired for use in more strenuous activities. Four to six inch widths are preferred for most uses.

As shown, the free end portion 20 and the outer surface of the webbing strap 16 nearer to the buckle 22 are respectively provided with strips 24 and 26 of suitable synthetic materials which adhere when pressed together such as sold under the trademark "Velcro" so as to provide an infinitely adjustable and secure buckling arrangement for applying a wide range of selective tensile loadings on the webbing 12. Of course, other type buckling arrangements may be suitably employed for providing the desired selectivity in belt rigidity. For example, a double loop-type buckle is such a buckling arrangement wherein the free end portion 20 can be looped between the two buckles and pulled for providing the desired and selective tightening of the belt about the waist of the user. Further "seat belt"-type buckling arrangements also may be utilized.

Figure 2:
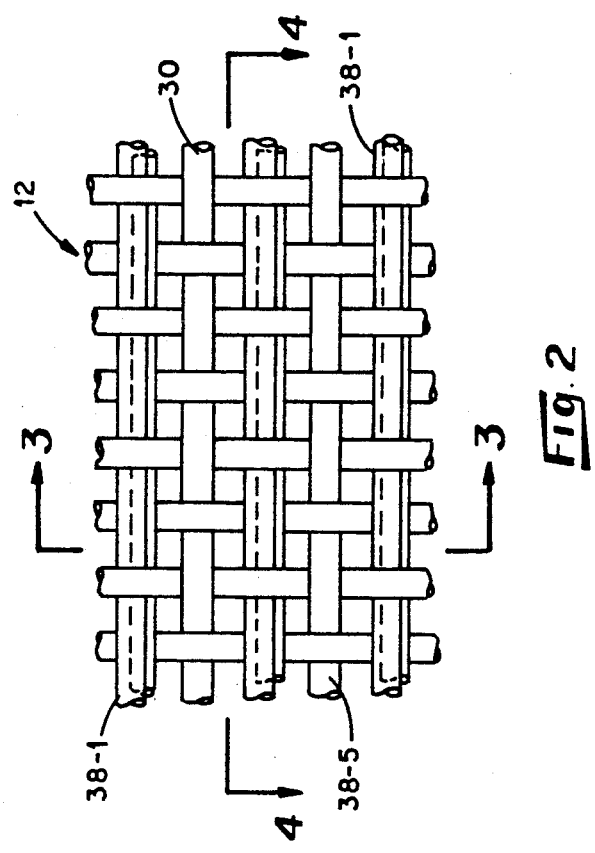
FIG. 2 is an enlarged and expanded fragmentary plan view taken along lines 2—2 of FIG. 1 showing a plain weave pattern used for forming the webbing utilized in the construction of the depicted support belt of the present invention.
Figure 3:
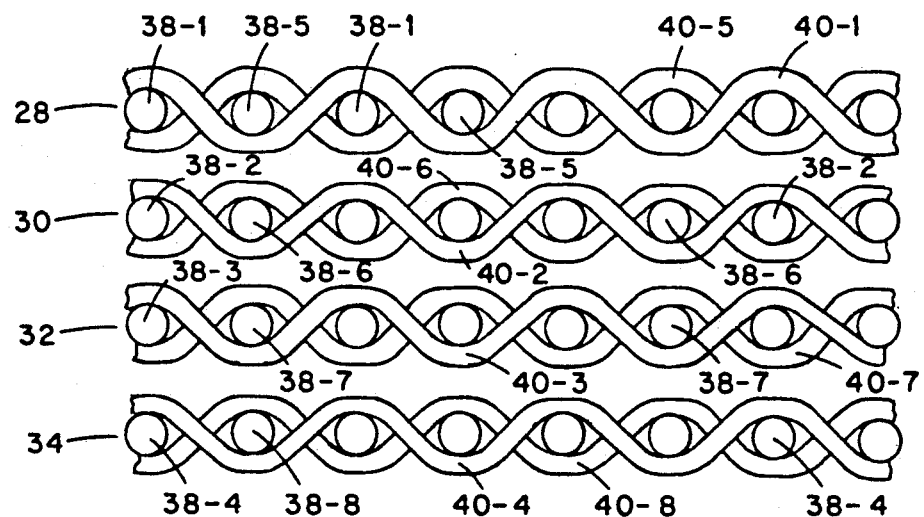
FIG. 3 is an enlarged and expanded fragmentary end view of the support belt of the present invention as taken along lines 3—3 of FIG. 2 and generally showing a belt of multiple-ply thickness as provided by a four-ply, plain weave, belt webbing.
Figure 4:
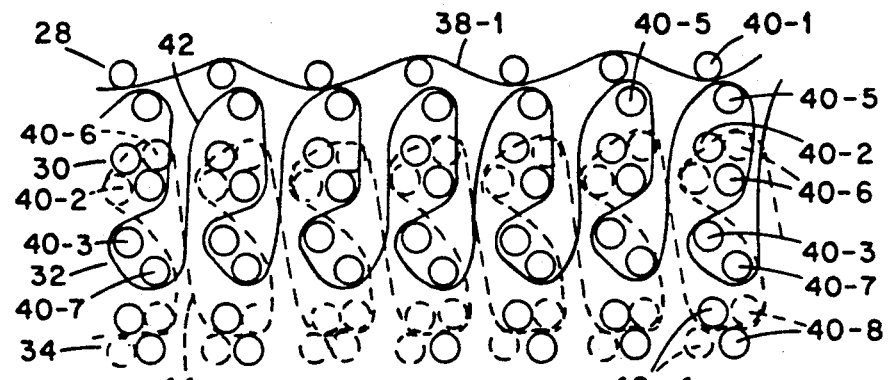
FIG. 4 is an enlarged and expanded fragmentary end view taken generally along lines 4—4 of FIG. 2 and illustrating the interconnection of the webbing plies by longitudinally extending binder yarns that extend from the top and bottom plies of the four-ply webbing and respectively engage weft yarns in underlying and overlying plies intermediate the top and bottom plies to form the hinge arrangement used for belt rigidity control in accordance with the present invention.

The webbing 12 forming the main body of the belt 10, as best illustrated in FIGS. 2-4, is shown formed of a four-ply webbing 12 with each ply 28, 30, 32, and 34 being formed by interlacing or weaving of warp yarns with weft yarns in a tight, plain weave pattern. The weaving of the webbing 12 and the other webbings used in the construction of the belt 10 may be accomplished in any suitable loom having the capability of providing the desired weave pattern, such as the plain weave preferred for the formation of the webbing 12, and the weave pattern for the binder yarns used for tying the plies together and providing the belt rigidifying hinge effect. The weave in each ply of the webbing is a relatively tight weave such as provided by a fairly aggressive lay motion of the reed during the weaving operation.

The warp yarns used in the webbing 12 are indicated by numerals 38-1 through 38-8. The warp yarns in the webbing ply 28 forming the face 18 of the belt 10 are indicated by numerals 38-1 and 38-5. The warp yarns in the webbing ply 34 forming the backside or the inner surface of the webbing 12 are indicated by numerals 38-4 and 38-8. The warp yarns used in the central layers or plies 30 and 32 intermediate to the face ply 28 and the inner surface ply 34 are shown at 38-2 and 38-6 in the second ply 30 or the ply nearest the face ply 28 and at 38-3 and 38-7 in the third ply 32 or the ply nearest the inner surface ply 34 of the webbing 12.

The materials used for the formation of the warp yarn 38-1 through 38-8 may be of any suitable natural fiber, such as hemp, jute, cotton, etc., or synthetic polymeric material such as polypropylene, nylon, polyester, etc., the polymeric yarns being either monofilamentary or polyfilamentary, or even combinations of these. The warp yarns in the face ply 28 and the inner surface ply 34 of the webbing 12 are preferably formed of polypropylene, preferably multifilamentary, which provides strength while the yarns in the middle plies 30 and 32 are preferably formed of natural polyester, preferably multifilamentary, which provides bulk and strength. These warp yarns 38-1 through 38-8 may be of any satisfactory weight in the range of about 1500/1 to 2000/1 denier. A 1680/1 denier polypropylene yarn is preferred as the warp yarns for the face ply 28 and the inner surface ply 34. The warp yarns in the middle plies are preferably formed of 1000/4 denier natural polyester yarn. Of course, the weight and selection of the warp-yarn materials may be readily varied to provide the desired structure and rigidity range for the webbing 12. The warp yarns forming the face ply 28 and the inner surface ply 30 may be suitably colored to provide the belt 10 with an aesthetic color scheme. For example, the warp yarns in the face ply 28 may be black while the warp yarns in the inner surface ply 34 may be red so as to provide the belt 10 with a black/red color scheme. Other color schemes such as royal blue and pewter combinations may also be used. The warp yarns in the middle plies 30 and 32 may be of any suitable color, such as white, since they are not visible externally of the webbing 12.

The weft yarns in the webbing 12 as indicated by numerals 40-1 through 40-8 are interwoven with the warp yarns 38-1 through 38-8 in an alternating manner typical of a plain weave pattern with two weft yarns being used about each warp yarn in each ply in an alternating over and under weave pattern. The weft yarns may be formed of any suitable natural fiber, such as hemp, jute, cotton, etc. or synthetic material such as nylon, polyester, polypropylene, etc. Weft yarns in the range of about 400/1 to 450/1 may be selected to provide the transverse or semi-flexibility and lateral strength required for the belt. The weft yarns in all the plies are preferably provided by natural nylon of 420/1 denier.

When using belt color schemes such as described above, the weft yarns may be white since portions of the weft yarns in the face ply 28 and the inner surface ply 34 are readily visible on the exposed surfaces of the belt and provide some enhancement to the aforementioned color schemes.

As best shown in FIGS. 2 and 4, the four plies of the webbing 12 are tied together by a binder yarn weave pattern which acts like a hinge between the plies to pull and press the plies of the webbing closer together and simultaneously to pull the weft yarns closer together when a longitudinal tensile loading is applied to the webbing 12 such as provided by tightening the belt 10 about the waist of a user. The binder yarns have been omitted from FIG. 3 and the warp yarns in plies 30, 32, and 34 have been omitted from FIG. 4 for ease of illustration. Further it is to be recognized that FIG. 4 represents a view taken along a plane that extends transversely of the length of the webbing 12, and that the weft yarns 40-1 and 40-5 alternate positions (up or down) as the plane is moved along the length of the webbing 12. The binder weave yarns may be suitably provided by employing a plurality of longitudinally extending binder yarns each of which is coextensive with the warp yarns and which is positioned at a location between each pair of warp yarns. A first set of binder yarns 42 is interwoven between, and tie together, the plies 28, 30 and 32, and a second set of binder yarns 44 are interwoven between, and tie together, the plies 30, 32 and 34, thereby interconnecting all the plies.

As shown in FIG. 4, the binder yarns 42 extend over the weft yarns 40-5 and under the weft yarns 40-1 in the face ply 28 of the webbing 12 and encircle the weft yarns 40-3 and 40-7 in the third layer or ply 32 of the webbing 12 vertically underlying weft yarns 40-5 in the face ply 28 before returning to the face ply 28 for passage over the next adjacent weft yarn 40-5 in the face ply 28 of the webbing 12. This weave pattern for the binder yarns 42 is repeated in a serial manner throughout the length of the webbing 12. Also, as indicated by the dotted lines in FIG. 4, the binder yarns 44 located intermediate each pair of the warp yarns 38-4 and 38-8 (see FIG. 3 also) of the inner surface ply 34 of the webbing 12 extend over the weft yarns 40-8 and under the weft yarns 40-4 in the inner webbing surface ply 34 and encircle the weft yarns 40-2 and 40-6 in the second ply 30 vertically overlying the weft yarns 40-4 in the inner surface ply 34 and return to the inner webbing surface over the top of the next adjacent weft yarns 40-8 with this weave pattern being repeated in a serial manner throughout the length of the webbing 12. As illustrated by the solid and dotted lines in FIG. 4, the binder yarns 42 and 44 alternately engage the weft yarns in the intermediate plies 30 and 32 of the webbing along the transverse width of the webbing 12. The yarn used for the binding yarns 42 and 44 may be, and is preferably, like or similar to that employed in the warp yarns in the face ply 28 and the inner surface ply 34 of the webbing 12. The tension loading applied on the binder yarns 42 and 44 during the weaving operation serves to foreshorten the binder yarns, hence to pull the plies and the weft yarns together into a contiguous relationship that imparts lateral rigidity to the belt beyond that which the binder yarns normally provide in a relaxed state following the weaving operation. Importantly, however, due to the hinge effect of the binder yarns, the belt retains its ability to bend about its longitudinal dimension and conform to the body of the user to provide the desired close fit and resultant support to the body of the user. The tensile loading on the binder yarns is chosen to assure a tight weave. As noted, the interlacing of the binder yarns 42 and 44 with the weft yarns in the inner plies 30 and 32 provides the hinge-like arrangement between the plies of the webbing 12 whereby a longitudinally applied tensile loading on the webbing 12 as provided by the belt user will pull on the binder yarns to draw and press the plies and weft yarns together and thereby increase the lateral rigidity of the webbing 12.

Alternatively, the binder yarns for the webbing 12 may be provided by employing alternately disposed warp yarns in the face ply 28 and the inner surface ply 34 of the webbing 12 in the weave pattern shown in FIG. 3. In such a case, for example, the warp yarns 38-5 and 38-8 would be interwoven with the weft yarns in the intermediate plies to provide the joining of the webbing plies and the rigidity-producing hinge action of the present invention. This weave pattern would appear similar to that shown in FIG. 4 for the separate binder yarns. Thus, the FIG. 4 illustration is considered for the purposes of this description to be illustrative of the warp yarns being used as the binding yarns.

Figure 5:
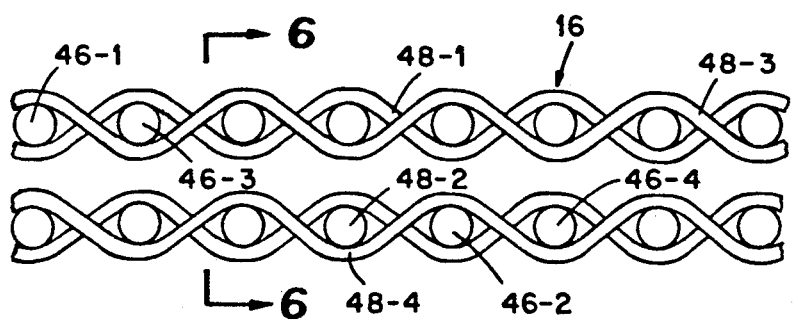
FIG. 5 is an enlarged and expanded fragmentary end view taken along lines 5—5 of FIG. 1 for showing details of a two-ply webbing construction utilized in a strap attached to the main belt webbing as illustrated in FIG. 1 and used for fastening the belt around the waist of the user and for applying a tensile loading on the warp yarns and binder yarns in the main belt webbing.
Figure 6:
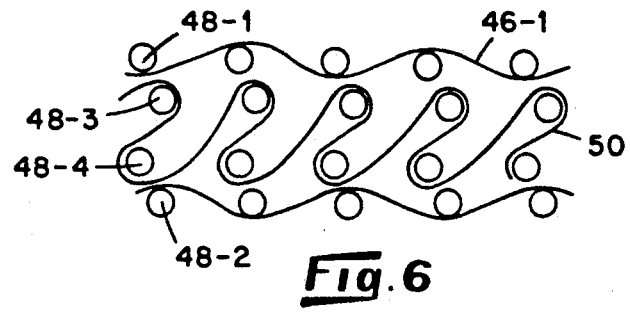
FIG. 6 is an enlarged and fragmentary end view taken along lines 6—6 of FIG. 5 for showing the binder yarn interconnection between the two plies of the strap webbing as provided by binder yarns in one ply engaging weft yarns in the other ply.

With reference to FIGS. 5 and 6, the strap webbing 16 used for buckling the belt about the waist of the user may be formed of a two-ply plain weave construction with the warp yarns in the top layer indicated by numerals 46-1 and 46-3 and the warp yarns in the bottom layer indicated by numerals 46-2 and 46-4. The weft yarns alternately woven about the warp yarns are indicated by numerals 48-1 through 48-4. The two-plies of the strap webbing 16 are tied together by binder yarns in a weave pattern substantially similar to that used in the webbing 12. For example, as shown in FIG. 6, the longitudinally extending binder yarns 50 are looped about the weft yarns in the top ply or the outer ply and the weft yarns in the inner ply to pull the two plies together. As with the main webbing 12, the weave pattern used for the binder yarns in the strap webbing 16 provides increased lateral rigidity of the strap webbing 12 and a hinge-like action between the plies during the application of longitudinal tensile loadings.

Alternatively, as with the webbing 12, the binder yarns in the strap webbing 16 may be provided by employing alternately disposed warp yarns in the outer or inner ply of the strap webbing 16. For the purposes of this description, FIG. 6 is deemed to be illustrative of this weave pattern employing alternately disposed warp yarns as the binder yarns.

The weave pattern for the binder yarns and the warp yarns when used as the binder yarns is essentially similar to that employed in the webbing 12. The yarn materials and the weight of the yarns used in the strap webbing 16 may be selected from the yarn materials and yarns weights used for forming the webbing 12. Preferably, in the strap webbing 16 the warp yarns, the weft yarns, and the binding yarns are formed of 840/1 denier polypropylene. These yarns in the strap webbing 16 may be colored to correspond or contrast with the color scheme of the webbing 12.

The width of the strap webbing 16 is selected to be sufficient to apply an adequate tensile loading onto the webbing 12 to effectively control the lateral rigidity of the belt within a desired range and also be of comfort to the user. A strap webbing 16 having a width in a range of about 1 to 4 inches is sufficient to be used on the belts envisioned by the present invention with the wider strap webbing 16 being used on the wider belts to assure that adequate tensile loadings can be applied on the webbing 12 to provide the desired hinging effect and rigidity control in the belt. Also, while the strap webbing 16 is shown in FIG. 1 as extending over the full length of the belt 10 it will appear clear that a central section of the strap webbing 16 can be removed and still retain the desired and selective control over the rigidity in the belt.

It will be seen that the present invention provides a semi-flexible belt wherein the control of the belt rigidity is adjustable over a wide range of rigidity levels so as to provide a single belt usable in a number of activities where different levels of belt rigidity are required. The user by simply adjusting the longitudinal tension on the belt by tightening the belt or by loosening a previously tightened belt may readily control the rigidity of the belt so as to be of comfort to the user due to retention of the semi-flexible properties of the belt and yet provide adequate back support to alleviate back strain problems encountered in many activities.

What is claimed is:

1. An elongated semi-flexible woven support belt having selective rigidity control, comprising a webbing formed of a plurality of contiguous plies of woven yarns with each ply comprising a plurality of longitudinally extending warp yarns interwoven with a plurality of transversely extending weft yarns, binder yarn means comprising a plurality of longitudinally extending yarns engaging selective weft yarns in the several plies of said webbing and coupling together said plies and any plies therebetween and providing hinge means whereby a longitudinally applied tensile loading on said webbing urges said plies together to increase the rigidity of the webbing, and adjustable means carried by said webbing for applying a selected longitudinal tensile loading on said webbing.

2. An elongated semi-flexible woven support belt as claimed in claim 1, wherein the adjustable means comprises a further longitudinally extending webbing of woven yarns fixedly attached to the first-mentioned webbing and buckle means affixed to said further webbing.

3. An elongated semi-flexible woven support belt as claimed in claim 2, wherein said further webbing is at least coextensive with the first-mentioned webbing.

4. An elongated semi-flexible woven support belt as defined in claim 3, wherein said further webbing includes an end portion unattached to the first-mentioned webbing and engageable with said buckle means for applying said selected longitudinal tensile loading on the first-mentioned webbing.

5. An elongated semi-flexible woven support belt as claimed in claim 4, and including adhering means carried by said unattached end portion, and a portion of said further webbing which is attached to the first-mentioned webbing receiving said adhering means for securing said end portion to the attached portion of the said further webbing.

6. An elongated semi-flexible woven support belt as defined in claim 2, wherein said further webbing comprises a plurality of contiguous plies of woven yarns with each ply comprising a plurality of longitudinally extending warp yarns interwoven with transversely extending weft yarns, and including further binder yarn means comprising a plurality of longitudinally extending yarns engaging selected weft yarns of said plies and coupling together said plies.

7. An elongated semi-flexible woven support belt as defined in claim 6, wherein the plurality of plies forming the first-mentioned webbing comprises two surface plies, and wherein said binder yarn means in the first-mentioned webbing are coextensive with the warp yarns in at least one of said surface plies.

8. An elongated semi-flexible woven support belt as claimed in claim 7, wherein the plurality of plies forming the first-mentioned webbing includes at least one further ply disposed intermediate said surface plies, and wherein the binder yarn means engages weft yarns in at least one of said surface plies and weft yarns of said intermediate ply.

9. An elongated semi-flexible woven support belt as defined in claim 2, wherein the plies in said further webbing are in a plain weave pattern.

10. An elongated semi-flexible woven support belt as defined in claim 2, wherein the woven yarns in said further webbing comprise warp yarns and weft yarns formed of polymeric material respectively similar to the polymeric material forming the warp yarns and the weft yarns in the first-mentioned webbing.

11. An elongated semi-flexible woven support belt as defined in claim 2 wherein said further webbing is of a width in the range of about two to about three inches.

12. An elongated semi-flexible woven support belt as defined in claim 1, wherein the plurality of plies forming the first-mentioned webbing comprises two surface plies, and wherein said binder yarn means in the first-mentioned webbing are coextensive with the warp yarns in at least one of said surface plies.

13. An elongated semi-flexible woven support belt as defined in claim 12, wherein said binder yarn means serially engages a plurality of longitudinally spaced apart weft yarns in said surface plies.

14. An elongated semi-flexible woven support belt as claimed in claim 12, wherein the plurality of plies forming the first mentioned webbing includes at least one further ply disposed intermediate said surface plies, and wherein the binder yarn means engages weft yarns in at least one of said surface plies and weft yarns of said intermediate ply.

15. An elongated semi-flexible woven support belt as defined in claim 1, wherein the plurality of plies forming the first-mentioned webbing comprises two surface plies and two plies disposed intermediate said surface plies, and wherein individual yarns of said binder yarn means engage weft yarns in a surface ply and the weft yarns in that intermediate ply nearest the other surface ply.

16. An elongated semi-flexible woven support belt as defined in claim 1, wherein said binder yarn means comprises a plurality of binder yarns separate from the warp in each of said plurality of plies forming the first-mentioned webbing.

17. An elongated semi-flexible woven support belt of claim 16 wherein each of the binder yarns is disposed in close proximity to alternately disposed warp yarns in said plies.

18. An elongated semi-flexible woven support belt as defined in claim 1, wherein said binder yarn means comprise alternately disposed warp yarns in said at least one of said surface plies.

19. An elongated semi-flexible woven support belt as defined in claim 1, wherein the plies in the first-mentioned webbing are of a plain weave pattern.

20. An elongated semi-flexible support belt as defined in claim 1, wherein said warp yarns comprise polymeric material selected from the group consisting of polypropylene, nylon, and polyester and of a weight in range of about 1500/1 to 2000/1 denier comprising between 10 and 100 filaments per end, and wherein the weft yarns comprise polymeric material selected from the group consisting of a natural polyester, polypropylene and nylon, and of a weight in the range of 400 to 450 denier comprising between about 56 and about 86 filaments per end.

21. An elongated semi-flexible woven support belt as defined in claim 1, wherein said webbing includes two to six contiguous plies of woven yarns.

22. An elongated semi-flexible woven support belt as defined in claim 1, wherein said webbing is of a width in the range of about two to about eight inches.

* * * * *